(12) United States Patent
Imani et al.

(10) Patent No.: US 6,498,952 B2
(45) Date of Patent: Dec. 24, 2002

(54) HERMETICALLY SEALED FEEDTHROUGH CONNECTOR USING SHAPE MEMORY ALLOY FOR IMPLANTABLE MEDICAL DEVICE

(75) Inventors: Ray Imani, Moorpark, CA (US); Clyde K. Nason, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 61 days.

(21) Appl. No.: 09/802,231

(22) Filed: Mar. 8, 2001

(65) Prior Publication Data

US 2002/0128692 A1 Sep. 12, 2002

(51) Int. Cl.[7] .............................................. A61N 1/375
(52) U.S. Cl. ........................................................ 607/37
(58) Field of Search .............................. 607/1, 4–5, 9, 607/36–38, 115–116, 119; 439/909

(56) References Cited

U.S. PATENT DOCUMENTS

| | | | |
|---|---|---|---|
| 4,913,147 A | * 4/1990 | Fahlstrom et al. | 607/2 |
| 4,934,366 A | 6/1990 | Truex et al. | 128/419 |
| 5,653,759 A | 8/1997 | Hogan et al. | 623/11 |
| 5,707,399 A | * 1/1998 | Killander et al. | 607/37 |
| 5,908,447 A | 6/1999 | Schroeppel et al. | 607/126 |
| 5,957,966 A | 9/1999 | Schroeppel et al. | 607/122 |
| 5,968,082 A | * 10/1999 | Heil | 607/37 |
| 6,102,753 A | * 8/2000 | Lindergren | 439/848 |
| 6,430,442 B1 | * 8/2002 | Peters et al. | 607/37 |

* cited by examiner

Primary Examiner—Kennedy Schaetzle
Assistant Examiner—Kristen Droesch

(57) ABSTRACT

A feedthrough connector for an implantable medical device includes a hermetically sealed housing containing an electrical circuit and a tubular barrel with an open end and a closed end defining a tubular channel that protrudes into the sealed housing while maintaining the seal of the housing. The inside of the tubular channel is open to the outside of the sealed housing through the open end and the tubular barrel also has a plurality of circumferentially spaced openings extending between an outer peripheral surface and the tubular channel. An electrical contact assembly electrically in common with the electrical circuit within the housing serves to make electrical contact with an electrical lead axially inserted into the open end of the tubular channel. The electrical contact assembly includes a plurality of contact members received in and projecting radially through a plurality of circumferentially spaced openings and a sleeve member of shape memory alloy freely overlies the contact members when in a first deformed-shape configuration but engage the contact members and the outer peripheral surface of the tubular barrel when in a second memory-shaped configuration, urging the contact members into mechanical, electrical, and hermetically sealed engagement with the electrical lead. The tubular channel may include a plurality of conductive cylindrical portions coaxial with the axis of the tubular barrel, the dimensions of the diameter of the successive cylindrical portions progressively decreasing from the open end to the closed end.

12 Claims, 3 Drawing Sheets

HERMETICALLY SEALED FEEDTHROUGH CONNECTOR USING SHAPE MEMORY ALLOY FOR IMPLANTABLE MEDICAL DEVICE

FIELD OF THE INVENTION

The present invention relates generally to an electrical connector used with an implantable medical device, such as a pacemaker, for stimulating selected body tissue for connecting an implantable electrical lead to the electrical circuits within a hermetically sealed housing of the medical device. More particularly, the present invention relates to a feedthrough connector assembly which employs shape memory alloy components for ease of manufacture and for assuring a hermetically sealed engagement with the electrical lead.

BACKGROUND OF THE INVENTION

Implantable electronic devices are in use providing electronic pulses to stimulate tissue via a lead extending from an implanted pulse generator to a desired internal location. An example of this type of technology is a pacemaker and a pacing lead which provides electrical stimulation to the heart. The pacemaker is usually implanted in a subcutaneous cavity, and the leads extend either transvenously to the internal cavities of the heart, or to patch electrodes located on external surface of the heart.

The leads generally include at least one, and often two or more, electrodes located at a distal end, and a connector having a similar number of electrical connector elements for interconnection to the pulse generator at the proximal end. The electrical connector elements, or contacts, at the proximal end and the distal electrodes are interconnected by conductors extending through an insulated lead body. It is common for the leads to include helically wound conductors which are either coaxially mounted or side-by-side wound within the lead body, separated by insulation.

The connector is inserted into a receiving orifice in a header portion of the pulse generator. The header portion of the pulse generator may be formed from an epoxy material which is assembled and bonded to the main body of the pulse generator. The main body of the pulse generator is generally a metallic self-contained housing or can, which encloses the source of electrical energy and electrical circuitry for controlling the electrical stimulus delivered by the lead.

In the design of the lead connector and the pulse generator, it is important for the lead to be safely secured to the pulse generator to prevent inadvertent decoupling. Generally, connectors have been assembled using flexible insulation materials to separate the respective electrical components. Problems which arise in the construction and use of multiple conductor lead connectors are primarily related to the design of the electrical interconnection between the conductors and the contacts. The connector must be constructed in a manner which prevents fluids from invading the connector and shorting the electrical conductors therein. At the same time, simpler constructions which reduce the number of components, speed the assembly process and assure that the resulting medical device is hermetically sealed are constantly being sought.

A number of patents are representative of the prior art in this regard.

U.S. Pat. No. 4,934,366 to Truex et al. discloses a feedthrough connector for an implantable medical device which combines the connector function with the feedthrough function and eliminates the need for the cast epoxy connector previously used on such devices.

U.S. Pat. No. 5,653,759 to Hogan et al. discloses an in-vivo methodology for repairing aruptureso fragmented segment of a pre-existing therapeutic appliance which has been previously surgically positioned or implanted within a human body. The repair methodology eliminates the need for surgical excision procedures by using a guiding catheter and deformable, thermoelastic shape-memory alloy rods in order to access and repair the flawed or failing therapeutic appliance.

U.S. Pat. Nos. 5,908,447 and 5,957,966 to Schroeppel et al. both disclose a cardiac lead that includes a connector for connecting to a cardiac stimulator and a flexible sleeve coupled to the connector. The sleeve has a first segment, a second segment, and a jacket coupling the first segment and the second segment. The jacket is composed of a shape-memory polymeric material which deforms diametrically in situ to selectively disconnect the first segment from the second segment. An electrode is coupled to the sleeve and a conductor is disposed in the sleeve and coupled to the connector for conveying electrical signals. The breakaway function of the jacket allows removal of all but a small portion of the lead without dissection of fibrous tissue. It was in light of the foregoing that the present invention was conceived and has now been reduced to practice.

SUMMARY OF THE INVENTION

A feedthrough connector for an implantable medical device includes a hermetically sealed housing containing an electrical circuit and a tubular barrel with an open end and a closed end defining a tubular channel that protrudes into the sealed housing while maintaining the seal of the housing. The inside of the tubular channel is open to the outside of the sealed housing through the open end and the tubular barrel also has a plurality of circumferentially spaced openings extending between an outer peripheral surface and the tubular channel. An electrical contact assembly electrically in common with the electrical circuit within the housing serves to make electrical contact with an electrical lead axially inserted into the open end of the tubular channel. The electrical contact assembly includes a plurality of contact members received in and projecting radially through a plurality of circumferentially spaced openings and a sleeve member of shape memory alloy freely overlies the contact members when in a first deformed-shape configuration but engage the contact members and the outer peripheral surface of the tubular barrel when in a second memory-shaped configuration, urging the contact members into mechanical, electrical, and hermetically sealed engagement with the electrical lead. The tubular channel may include a plurality of conductive cylindrical portions coaxial with the axis of the tubular barrel, the dimensions of the diameter of the successive cylindrical portions progressively decreasing from the open end to the closed end.

The electrical contact assembly includes an annular spring member which overlies the plurality of circumferentially spaced openings in the tubular barrel and itself has a plurality of cicumferentially spaced holes generally aligned with the openings in the tubular barrel. The contact members are balls, each having a diameter greater than the diameter of the openings in the tubular barrel and greater than the diameter of the holes in the annular spring member. The balls are captured between the annular spring member and the tubular barrel and project through the holes for engagement with the electrical lead.

The annular spring member is discontinuous, having opposed finite ends capable of being separated against hoop bias from a closed position at which the finite ends are in a proximate relationship to an open position at which the finite ends are in a distant relationship for placement on the tubular barrel, then returned to the closed position when overlying the plurality of circumferentially spaced openings.

The tubular barrel has a pair of annular grooves in the outer peripheral surface longitudinally straddling the plurality of circumferentially spaced openings and lying in parallel spaced apart planes transverse of the tubular barrel axis. In a cooperative manner, the sleeve member has an inner peripheral surface with a pair of annular rims lying in parallel spaced apart planes aligned, respectively, with the annular grooves of the tubular barrel. With this construction, as the sleeve member assumes the second memory-shaped configuration, the annular rims of the sleeve member fittingly engage with the annular grooves of the tubular barrel and hermetically seal the region therebetween when the electrical lead is axially inserted into the open end of the tubular channel and sealingly engaged therewith.

Desirably, the tubular channel has an annular seal groove located intermediate successive cylindrical portions and includes an intermediate seal member received in the annular seal groove and engageable with the electrical lead when axially inserted into the open end of the tubular channel. In this manner, the circumferentially spaced openings associated with one cylindrical portion are isolated from the circumferentially spaced openings associated with the adjoining cylindrical portion.

In one instance, the tubular barrel is of dielectric material, ceramic for example, and includes an annular flange fixed to its open end which is welded to the housing of the implantable medical device. In this manner, the interior of the implantable medical device is hermetically sealed.

In another instance, the tubular barrel is of ceramic material and includes an integral first circular band spaced from its open end. A metallic tubular extension member is axially aligned with the tubular barrel and extends between first and second ends, the first end being proximate the tubular barrel, the tubular extension member having an annular flange at the second end, being an open end distant from the tubular barrel. The flange at the second end is welded to the housing of the implantable medical device and the tubular extension member includes an integral second circular band spaced from the first end. A connection sleeve member of shape memory alloy freely overlies the tubular barrel and the tubular extension member between the first and second circular bands when in a first deformed-shape configuration and engages the tubular barrel and the tubular extension member when in a second memory-shaped configuration to thereby firmly join the tubular barrel to the implantable medical device.

In each mentioned instance, the sleeve member assumes the first deformed-shape configuration above a predetermined temperature and assumes the second memory-shaped configuration below the predetermined temperature.

A primary feature, then, of the present invention is the provision of an improved feedthrough connector for an implantable medical device providing stimulating pulses to selected body tissue.

Another feature of the present invention is the provision of such a feedthrough connector for connecting an implantable electrical lead to the electrical circuits within a hermetically sealed housing of the medical device.

Yet another feature of the present invention is the provision of such a feedthrough connector which employs shape memory alloy components for ease of manufacture and for assuring a hermetically sealed engagement with the electrical lead.

Still another feature of the present invention is the provision of such a feedthrough connector which is assembled in a low heat sealing process using a shape memory alloy.

Yet another feature of the present invention is the provision of such a feedthrough connector which employs a reduced number of components when compared with known feedthrough connector constructions.

Still a further feature of the present invention is the provision of such a feedthrough connector using a shape memory alloy which requires only simple installation tooling, is performed at relatively low temperatures, results in a finished product which exhibits a low leakage rate, and allows sealing of dissimilar materials, such as titanium and non-methodized ceramic base.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
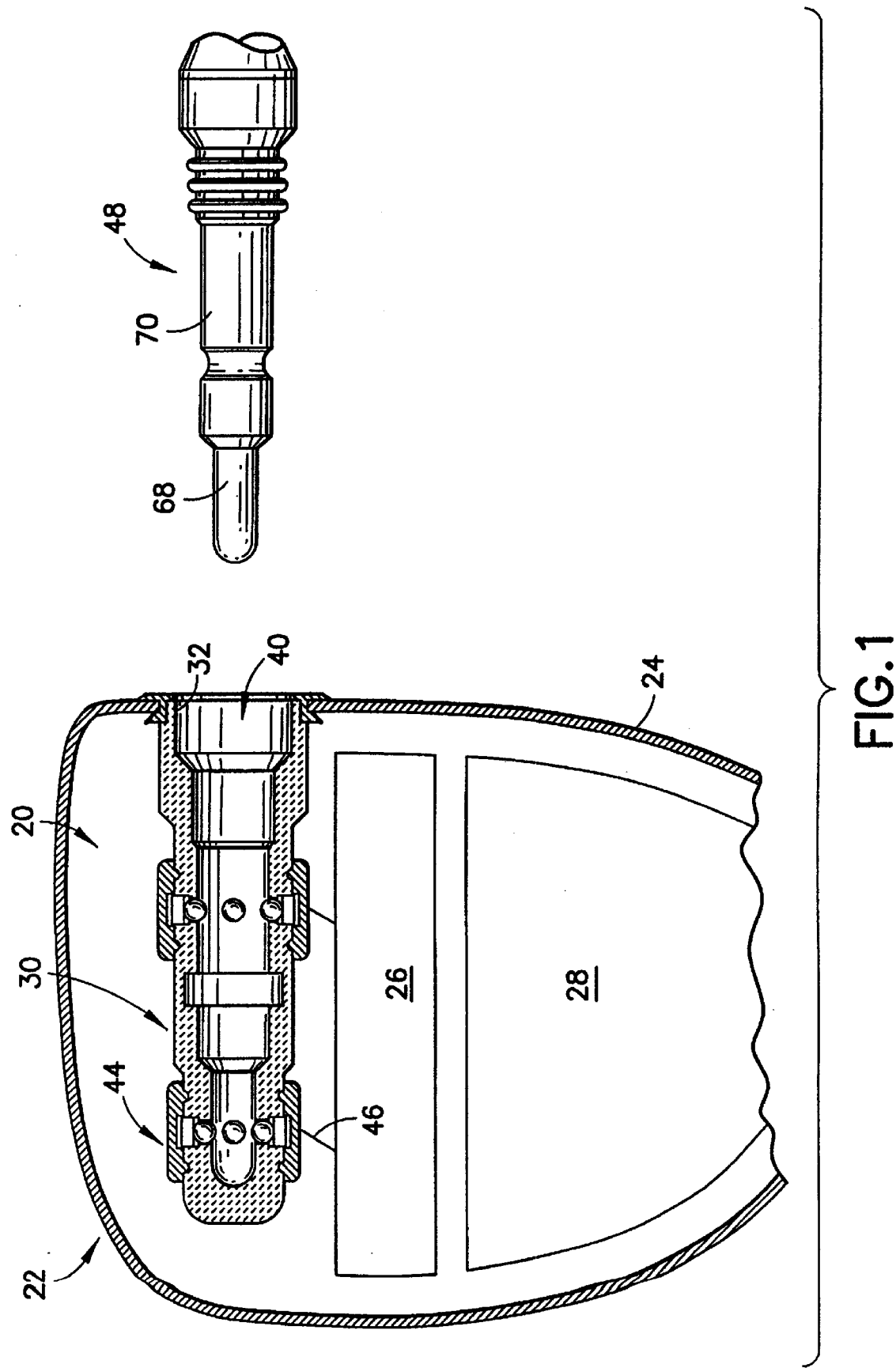
FIG. 1. is an exploded side elevation view, generally in section, illustrating an implantable medical device containing a feedthrough connector embodying the invention and into which an electrical lead is about to be inserted.

Turn now to the drawings and, initially to FIG. 1 which generally illustrates a feedthrough connector 20 for an implantable medical device 22, such as a pacemaker, including a hermetically sealed housing 24 and an electrical circuit 26 within the housing powered by a suitable battery 28. Although the present invention will be described with reference to the embodiments shown in the drawings, it should be understood that the present invention can be embodied in many alternate forms or embodiments. In addition, any suitable size, shape or type of elements or materials may be used.

Figure 2:
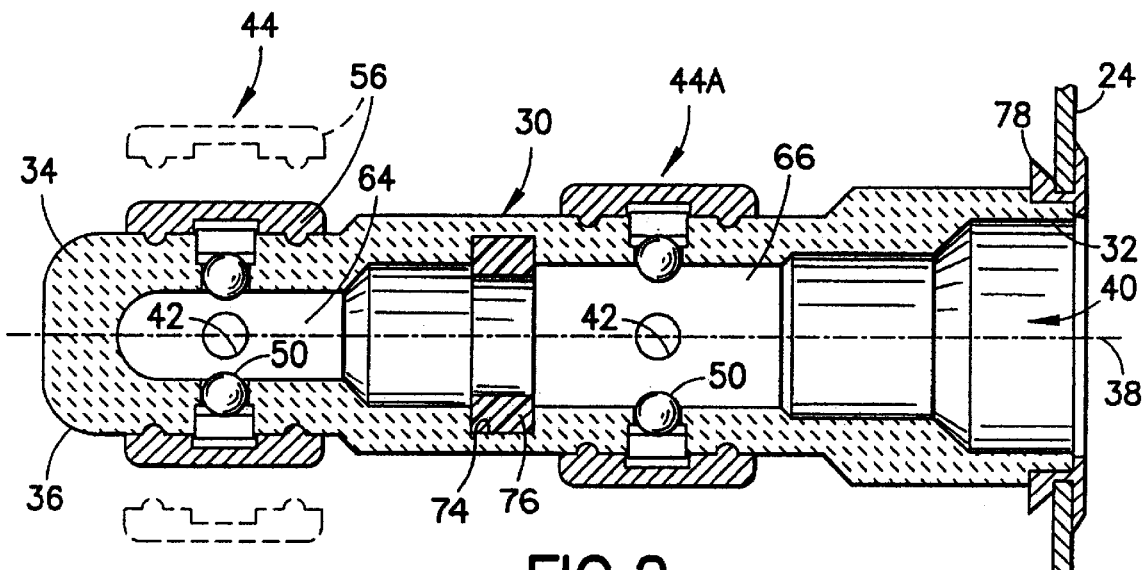
FIG. 2. is a detail cross section view of the feedthrough connector illustrated in FIG. 1.
Figure 3:
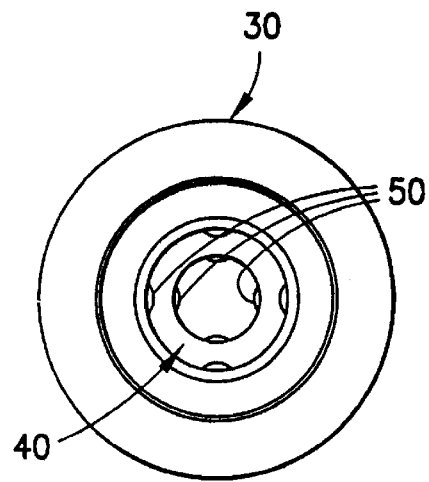
FIG. 3 is an end elevation view of the feedthrough connector illustrated in FIG. 2.
Figure 4:
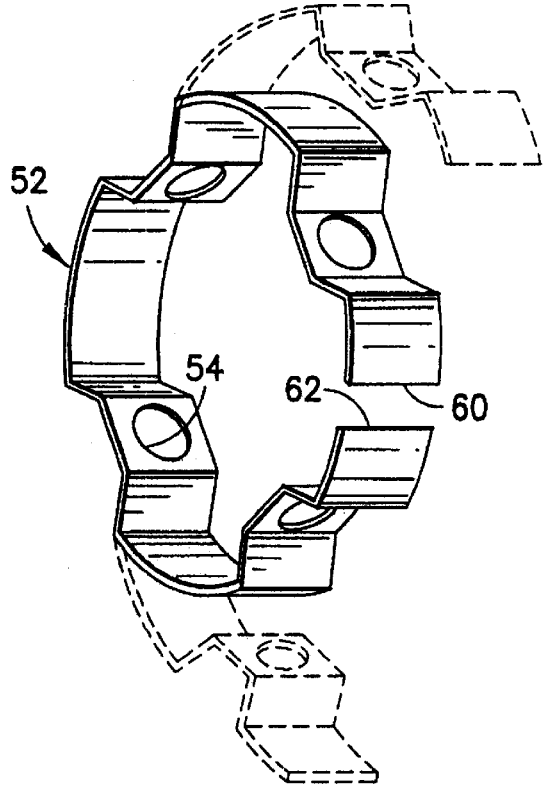
FIG. 4 is a detail perspective view of a component of the feedthrough connector illustrated in FIG. 2.
Figure 5:
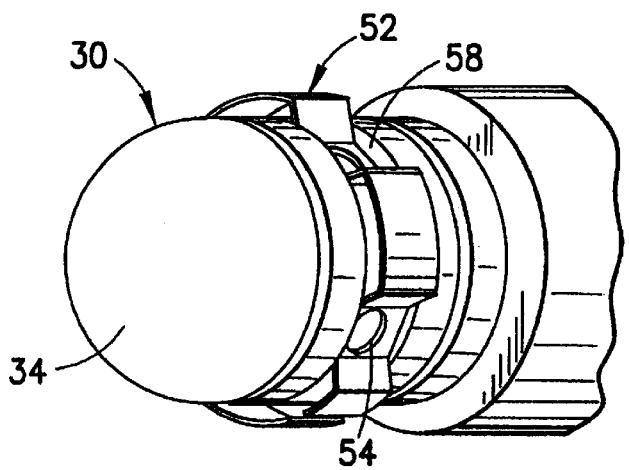
FIG. 5 is a perspective view of a portion of the feedthrough connector to which the component illustrated in FIG. 4 has been attached.

As best seen in FIGS. 2 and 3, the feedthrough connector 20 includes a tubular barrel 30 having an open end 32, a closed end 34, an outer peripheral surface 36, a longitudinally extending tubular barrel axis 38 passing through the open end and the closed end. The tubular barrel 30 defines a tubular channel 40 that protrudes into the sealed housing while maintaining the seal of the housing. The inside of the tubular channel 40 is open to the outside of the sealed housing through the open end 32. The tubular barrel 30 also has a plurality of circumferentially spaced openings 42 extending between the outer peripheral surface 36 and the tubular channel 40.

An electrical contact assembly 44 on the tubular barrel 30 is electrically joined with the electrical circuit 26, via an electrical conductor 46 (FIG. 1) and with an electrical lead 48,axially inserted into the open end 32 of the tubular channel 40. As best seen in FIGS. 2, 4, 5, and 6, the electrical contact assembly 44 includes a plurality of contact members in the form of metal balls 50 received in and projecting radially through the plurality of the circumferentially spaced openings 42. The electrical contact assembly also includes an annular spring member 52 which overlies the plurality of circumferentially spaced openings 42 in the tubular barrel 30 and has a plurality of cicumferentially spaced holes 54 generally aligned with the openings 42 in the tubular barrel. Each of the balls 50 has a diameter greater than the diameter of the openings 42 in the tubular barrel 30 and greater than the diameter of the holes 54 in the annular spring member 52. The balls 50 are thereby captured between the annular spring member 52 and the tubular barrel 30 and project through the holes 42 for engagement with the electrical lead 48.

To complete the description of the construction of the electrical contact assembly 44, a sleeve member 56 of shape memory alloy freely overlies the contact members or balls 50 when in a first deformed-shape configuration (indicated by dashed lines and is in firm engagement with the contact members and with the outer peripheral surface 36 of the tubular barrel 30 when in a second memory-shaped configuration (indicated by solid lines). In the latter configuration, the sleeve member 56 urges the contact members 50 into mechanical and electrical engagement with the electrical lead 48 when axially inserted into the open end 32 of the tubular channel 40. Further, the sleeve member 56 is drawn into firm hermetically sealed engagement with the outer peripheral surface 36 of the tubular barrel.

For attachment of the annular spring member 52 to the tubular barrel 30, the tubular barrel is formed with an annular recess 58 which is coplanar with the circumferentially spaced openings 42. The annular recess 58 has a width which is slightly larger than that of the annular spring member 52. As seen especially well in FIG. 4, the annular spring member is discontinuous, having opposed finite ends 60, 62 capable of being separated against hoop bias from a closed position, indicated by solid lines, at which the finite ends are in a proximate relationship to an open position, indicated by dashed lines, at which the finite ends are in a distant relationship for placement on the tubular barrel 30. In this opened position, the spring member 52 is moved radially into engagement with the annular recess 58, then returned to the closed position when overlying the plurality of circumferentially spaced openings 42. The balls 50 are positioned in associated openings 42 and holes 54 as the spring member 52 is returned to the closed position.

It will be appreciated that the tubular channel may include a plurality of cylindrical portions, 64, 66, for example, coaxial with the axis 38 of the tubular barrel 30. As seen in FIG. 2, the dimensions of the diameter of the successive cylindrical portions 64, 66 decrease progressively from the open end 32 to the closed end 34. This construction serves to accommodate the congruently formed electrical lead 48. The tubular barrel 30 has a plurality of the circumferentially spaced openings 42 at each of the cylindrical portions 64, 66 and a plurality of electrical contact assemblies 44, 44A are provided for making electrical contact between the cylindrical portions 64, 66 of the tubular channel and associated cylindrical portions 68, 70 of the electrical lead 48 when axially inserted into the open end 32 of the tubular channel 40. As previously explained, each electrical contact assembly 44, 44A includes a plurality of sets of contact members or balls 50 received in and projecting through the openings 42 for engagement with the respective cylindrical portions 64, 66 of the electrical lead 48.

Figure 6:
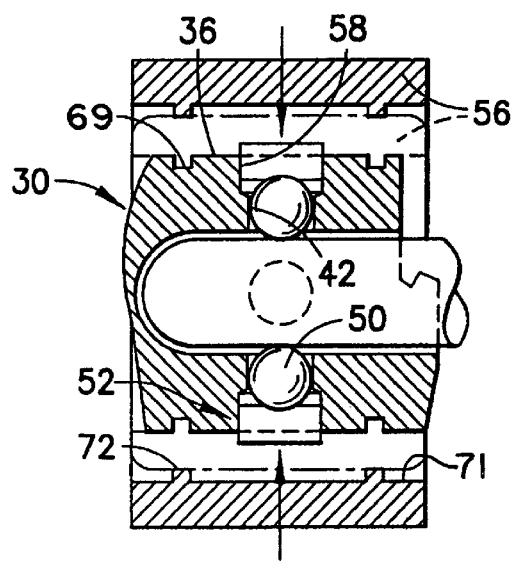
FIG. 6 is a detail cross section view of a portion of the feedthrough connector illustrated in FIG. 2.

With particular reference to FIG. 6, it can be seen that the tubular barrel has a pair of annular grooves 69 in the outer peripheral surface 36 longitudinally straddling the plurality of circumferentially spaced openings 42 and lying in parallel spaced apart planes transverse of the tubular barrel axis 38. In a similar fashion, the sleeve member 56 has an inner peripheral surface 71 with a pair of annular rims 72 lying in parallel spaced apart planes aligned, respectively, with the annular grooves 69 of the tubular barrel. With this construction, as the sleeve member 56 assumes the second memory-shaped configuration (in dashed lines in FIG. 6), the annular rims 72 of the sleeve member fittingly engage with the annular grooves 69 of the tubular barrel 30 and hermetically seal the adjoining region within the tubular barrel when the electrical lead 48 is axially inserted into the open end of the tubular channel and sealingly engaged therewith.

Returning momentarily to FIG. 2, the tubular channel 40 is seen to have an annular seal groove 74 located intermediate the successive cylindrical portions 64, 66, or at least intermediate the electrical contact assemblies 44, 44A. An intermediate seal member 76 is received in the annular seal groove 74 for engagement with the electrical lead 48 when axially inserted into the open end of the tubular channel 40. The seal member 76 serves to isolate the circumferentially spaced openings 42 associated with one cylindrical portion 64 from the circumferentially spaced openings associated with the adjoining cylindrical portion 66.

The tubular barrel 30 is of dielectric material, typically, ceramic and, as seen in FIG. 2, includes a metallic, typically titanium, annular flange 78 fixed, as by way of brazing, to the open end 32 and welded to the housing 24 of the implantable medical device 22 to thereby he metically seal the interior of the implantable medical device.

Figure 7:
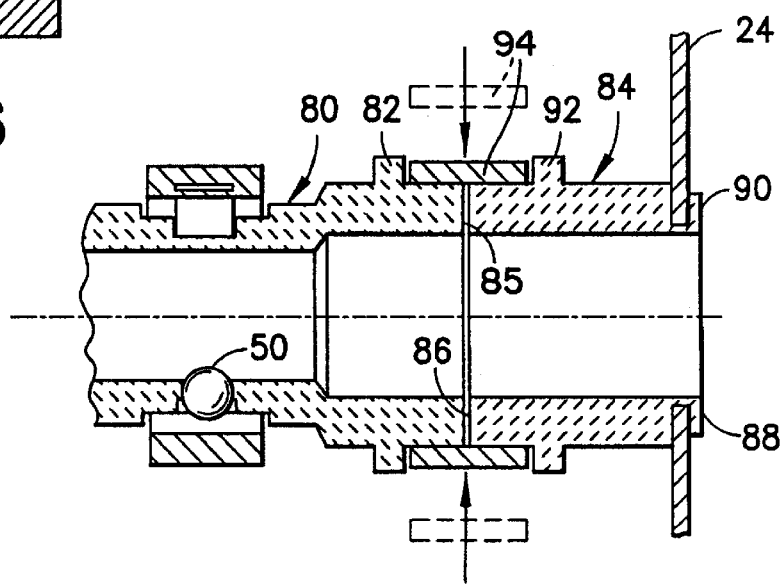
FIG. 7 is a detail cross section view, similar to a portion of FIG. 2 illustrating another embodiment of the invention.

In another instance, as seen in FIG. 7, a modified tubular barrel 80 of ceramic material includes an integral circular band 82 spaced from its open end 84. A tubular extension member 85 is axially aligned with the modified tubular barrel and extends between first and second ends, 86, 88, the first end being proximate the tubular barrel 80. The tubular extension member 85 has an annular flange 90 at the second end 88, being an open end, distant from the tubular barrel 80. The flange 90 at the second end 88 is welded to the housing 24 of the implantable medical device 22. The tubular extension member 85 also includes an integral second circular band 92 spaced from the first end 86.

A connection sleeve member 94 of shape memory alloy freely overlies the tubular barrel 80 and the tubular extension member 85 between the circular bands 82, 92 when in a first deformed-shape configuration, as indicated by dashed lines, connection sleeve member 94 of shape memory alloy freely overlies the tubular barrel 80 and the tubular extension member 85 between the circular bands 82, 92 but is spaced from those components when in a first deformed-shape configuration, as indicated by dashed lines. However, when the connection sleeve member assumes a second memory-shaped configuration, as indicated by solid lines, it is drawn into engagement with the tubular barrel and with the tubular extension member to thereby firmly join the tubular barrel to the implantable medical device.

It should be appreciated that FIG. 7 presents a new and improved manner of joining the tubular barrel 80 to the housing 24 as compared to the FIG. 2 manner of joining the tubular barrel 30 to the housing 24. Specifically, in FIG. 2, a conventional brazing process is employed which can result in the imposition of thermal stresses on the assembly. In contrast, in the instance of FIG. 7, elevated temperatures are not required but the shape memory alloy is used to create a hermetically sealed joint without thermal stresses being imposed on the assembly.

Throughout this disclosure, it will be understood that the sleeve members 56 and 94 assume the first deformed-shape configuration when heated to a temperature above a predetermined temperature and assumes the second memory-shaped configuration when cooled to a temperature below the predetermined temperature. Typically, the memory-shaped configuration would be attained when the assembly is subjected to the temperature of the human body.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A feedthrough connector for an implantable medical device including a hermetically sealed housing and an electrical circuit within the housing, the feedthrough connector comprising:

a tubular barrel having an open end, a closed end, an outer peripheral surface, a longitudinally extending tubular barrel axis passing through the open end and the closed end, the tubular barrel defining a tubular channel that is adapted to protrude into the sealed housing while maintaining the seal of the housing, the inside of the tubular channel being open to the outside of the sealed housing through the open end, the tubular barrel also having a plurality of circumferentially spaced openings extending between the outer peripheral surface and the tubular channel; and an electrical contact assembly on the tubular barrel that is adapted to be electrically in common with the electrical circuit within the housing for making electrical contact with an electrical lead axially inserted into the open end of the tubular channel, the electrical contact assembly including a plurality of contact members received in and projecting radially through the plurality of circumferentially spaced openings and a sleeve member of shape memory alloy freely overlying the contact members when in a first deformed-shape configuration and in engagement with the contact; members and with the outer peripheral surface of the tubular barrel when in a second memory-shaped configuration and adapted to urge the contact members into mechanical, electrical, and hermetically sealed engagement with the electrical lead.

2. A feedthrough connector for an implantable medical device as set forth in claim 1:

wherein the tubular channel includes a plurality of conductive cylindrical portions coaxial with the axis of the tubular barrel, the dimensions of the diameter of the successive cylindrical portions progressively decreasing from the open end to the closed end, the tubular barrel also having a plurality of circumferentially spaced openings at each of the cylindrical portions extending between the outer peripheral surface and the tubular channel; and including:

a plurality of electrical contact assemblies for making electrical contact between selected cylindrical portions of the tubular channel and associated cylindrical portions of the electrical lead axially inserted into the open end of the tubular channel, each electrical contact assembly including a plurality of sets of contact members received in and projecting through circumferentially spaced openings in the tubular barrel and a sleeve member of shape memory alloy freely overlying the contact members when in a first deformed-shape configuration and in engagement with the contact members and with the outer peripheral surface of the tubular barrel when in a second memory-shaped configuration and urging the contact members into mechanical, electrical, and hermetically sealed engagement with the electrical lead.

3. A feedthrough connector for an implantable medical device as set forth in claim 1:

wherein the electrical contact assembly includes an annular spring member which overlies the plurality of circumferentially spaced openings in the tubular barrel and has a plurality of cicumferentially spaced holes generally aligned with the openings in the tubular barrel; and wherein the contact members are balls, each having a diameter greater than the diameter of the openings in the tubular barrel and greater than the diameter of the holes in the annular spring member, the balls being captured between the annular spring member and the tubular barrel and projecting through the holes for engagement with the electrical lead.

4. A feedthrough connector for an implantable medical device as set forth in claim 3:

wherein the annular spring member is discontinuous, having opposed finite ends capable of being separated against hoop bias from a closed position at which the finite ends are in a proximate relationship to an open position at which the finite ends are in a distant relationship for placement on the tubular barrel, then returned to the closed position when overlying the plurality of circumferentially spaced openings.

5. A feedthrough connector for an implantable medical device as set forth in claim 1:

wherein the tubular barrel has a pair of annular grooves in the outer peripheral surface longitudinally straddling the plurality of circumferentially spaced openings and lying in parallel spaced apart planes transverse of the tubular barrel axis; and wherein the sleeve member has an inner peripheral surface with a pair of annular rims lying in parallel spaced apart planes aligned, respectively, with the annular grooves of the tubular barrel;

such that as the sleeve assumes the second memory-shaped configuration, the annular rims of the sleeve member fittingly engage with the annular grooves of the tubular barrel and hermetically seal the region therebetween when the electrical lead is axially inserted into the open end of the tubular channel and sealingly engaged therewith.

6. A feedthrough connector for an implantable medical device as set forth in claim 2:
wherein the tubular channel has an annular seal groove located intermediate successive cylindrical portions; and
including an intermediate seal member received in the annular seal groove and engageable with the electrical lead when axially inserted into the open end of the tubular channel to isolate the circumferentially spaced openings associated with one cylindrical portion from the circumferentially spaced openings associated with the adjoining cylindrical portion.

7. A feedthrough connector for an implantable medical device as set forth in claim 1:
wherein the tubular barrel is of dielectric material; and
wherein the tubular barrel includes an annular flange fixed to the open end thereof welded to the housing of the implantable medical device to thereby hermetically seal the interior of the implantable medical device.

8. A feedthrough connector for an implantable medical device as set forth in claim 7:
wherein the tubular barrel is of ceramic material.

9. A feedthrough connector for an implantable medical device as set forth in claim 1:
wherein the tubular barrel includes an integral first circular band spaced from its open end; and including:
a tubular extension member axially aligned with the tubular barrel and extending between first and second ends, the first end being proximate the tubular barrel, the tubular extension member having an annular flange at the second end, being an open end, distant from the tubular barrel, the flange at the second end being welded to the housing of the implantable medical device, the tubular extension member including an integral second circular band spaced from the first end; and
a connection sleeve of shape memory alloy freely overlying the tubular barrel and the tubular extension member between the first and second circular bands when in a first deformed-shape configuration and in engagement with the tubular barrel and the tubular extension member when in a second memory-shaped configuration to thereby firmly join the tubular barrel to the implantable medical device.

10. A feedthrough connector for an implantable medical device as set forth in claim 9:
wherein the tubular barrel is of dielectric material; and
wherein the tubular extension member is metallic.

11. A feedthrough connector for an implantable medical device as set forth in claim 1:
wherein the sleeve member assumes the first deformed shape configuration above a predetermined temperature and assumes the second memory-shaped configuration below the predetermined temperature.

12. A feedthrough connector for an implantable medical device as set forth in claim 1 including:
an electrical conductor electrically joining the sleeve member and the electrical circuit when the sleeve member is in the second memory-shaped configuration.

* * * * *